United States Patent [19]

Siri

[11] Patent Number: Plant 5,303

[45] Date of Patent: Oct. 23, 1984

[54] MINIATURE CARNATION

[75] Inventor: Angelo J. Siri, San Francisco, Calif.

[73] Assignee: Siri Brothers Nursery, Inc., East Palo Alto, Calif.

[21] Appl. No.: 397,114

[22] Filed: Jul. 12, 1982

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Limbach, Limbach & Sutton

[57] ABSTRACT

A miniature carnation with blossoms having white petals finely striped purple.

3 Drawing Figures

BACKGROUND OF THE NEW PLANT

This invention comprises a new and distinct miniature carnation variety that has its own set of characteristics that set it apart from all other varieties of miniature carnations. The newly discovered variety, called "Renée," originated as a sport of Apache, a patented variety, U.S. Plant Pat. No. 4,100.

The botanical classification of the new variety is *Dianthus caryophyllus Longicaulis.* The commercial classification is Miniature Carnation. The plant takes the form of a bush.

Asexual propagation of the newly discovered miniature carnation variety has been made at Siri Brothers Nursery, Inc. at East Palo Alto, Calif. by taking cuttings. The cuttings so taken and grown, have consistently produced flowers that have the new and distinct characteristics hereinafter described.

DESCRIPTION OF THE DRAWINGS

This new variety of miniature carnation plant is illustrated by the accompanying drawings which show the color characteristics of the flower as nearly true as it is reasonably possible to obtain through conventional photographic procedures.

DESCRIPTION OF THE NEW PLANT

The following detailed description of the new variety is based on my detailed observations of the new cultivar which were made at Siri Brothers Nursery Inc. at 940 O'Connor St., East Palo Alto, Calif. The response time, blooming period, total vigor, and color may vary slightly with varying environmental conditions such as temperature, length of day, and light intensity. The color description is given by designation "H" for hue and "L" for lightness in color chart references designated "LCC" for Limit Color Cascade, Munsell Color, Baltimore, Md. and "R.H.S." for Royal Horticultural Colour Chart, The Royal Horticultural Society, London, England.

FLOWER

Figure 1:
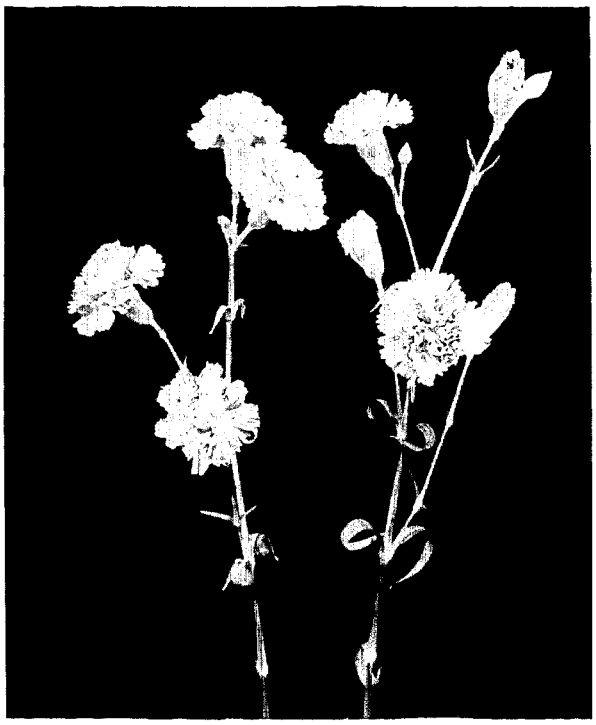
FIG. 1. PRIOR ART
FIG. 1 shows sprays and stems of the new variety Renee on the right and the prior Apache on the left.
Figure 2:
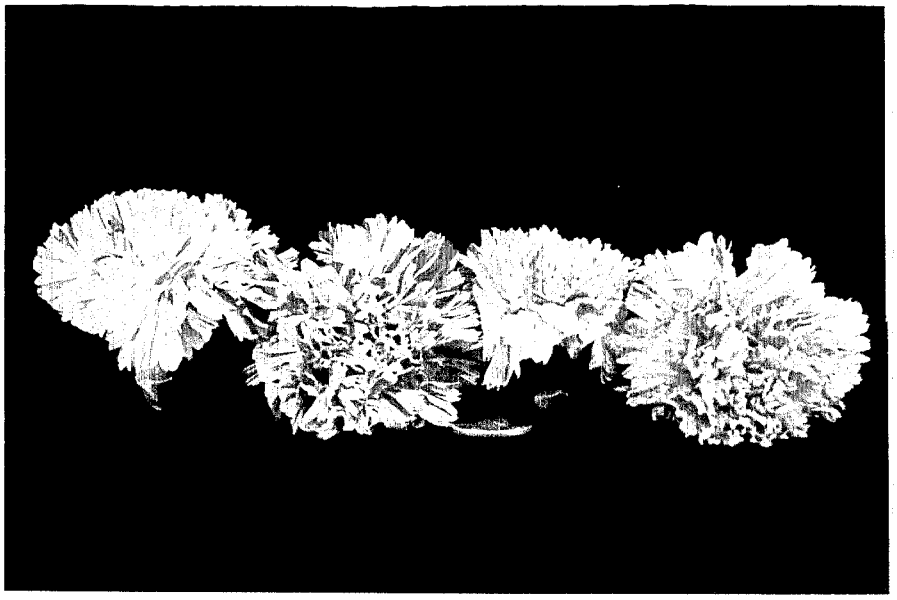
FIG. 2 shows the blooms of the new variety Renee on the right and the prior Apache on the left.
Figure 3:
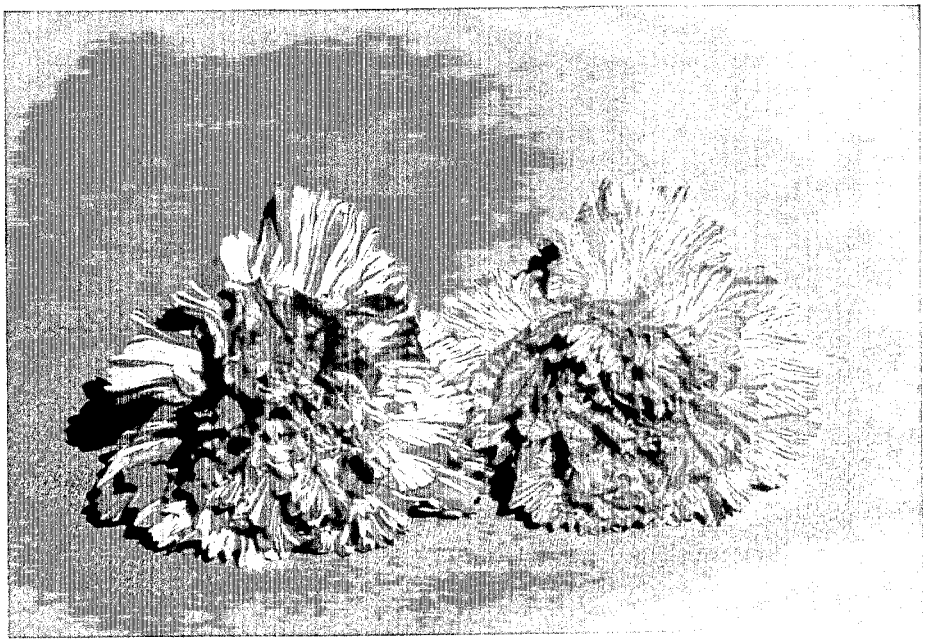
FIG. 3, while not showing the correct colors of the new variety and parent as those colors are correctly shown in FIGS. 1 and 2, shows the wide stripes of colors of the prior Apache on the left and the very thin lines of colors of the new variety on the right.

Description of the color of the bloom: The bloom is a pencil lined variegated purple (LCC H-43 L-14 top side and bottom side and LCC H-44 L-11 bottom side) and white (R.H.S. White Group 155D but brighter top side and bottom side). There are some larger purple and white lines but most are thin. The bloom appears as a thin lined variegated bloom. FIG. 3 shows the difference in the variegation of the prior Apache on the left and the new variety Renée on the right; the colors in FIG. 3 do not accurately correspond to the colors of the blooms which are better shown in FIGS. 1–2.

Topside of petal: Purple — LCC H-43 L-14, White — R.H.S. White Group 155D but brighter.

Underside of petal: Purple — LCC H-43 L-14 and LCC H-44 L-11, White — R.H.S. Group 155D but brighter.

DISTINGUISHING CHARACTERISTICS BETWEEN THE NEW VARIETY AND PARENT

The distinguishing characteristic is the type of variegation. The colors are the same. What is different is the way the colors are distributed on the petals. The parent, Apache, has large wide stripes of purple and white while the sport, Renée has very thin lines of purple and white variegation. This gives the sport, Renée a completely different appearance than the parent, Apache.

SIMILAR CHARACTERISTICS OF THE NEW VARIETY AND PARENT

All other characteristics other than the distinguishing one above are similar.

I claim:

1. A new and distinct varity of miniature carnation plant, substantially as herein shown and described.

* * * * *

PRIOR ART